United States Patent
Patton et al.

(10) Patent No.: US 9,322,523 B2
(45) Date of Patent: *Apr. 26, 2016

(54) ELECTRIC CANDLE HAVING A PLURALITY OF LIGHTS FOR SIMULATION OF A FLICKERING FLAME

(71) Applicant: Luminara Worldwide, LLC, Eden Prairie, MN (US)

(72) Inventors: Douglas Patton, Irvine, CA (US); Jeff Thompson, Orange, CA (US)

(73) Assignee: Luminara Worldwide, LLC, Eden Prairie, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/321,677

(22) Filed: Jul. 1, 2014

(65) Prior Publication Data

US 2014/0313694 A1   Oct. 23, 2014

Related U.S. Application Data

(63) Continuation-in-part of application No. 13/850,011, filed on Mar. 25, 2013, now Pat. No. 8,777,465.

(60) Provisional application No. 61/714,635, filed on Oct. 16, 2012.

(51) Int. Cl.
*F21S 10/04* (2006.01)
*F21V 21/002* (2006.01)
*F21V 23/06* (2006.01)
(Continued)

(52) U.S. Cl.
CPC ............. *F21S 10/046* (2013.01); *F21V 21/002* (2013.01); *A61L 9/032* (2013.01); *A61L 2209/12* (2013.01); *A61L 2209/133* (2013.01); *F21K 9/13* (2013.01); *F21V 23/06* (2013.01);
(Continued)

(58) Field of Classification Search
CPC ....... F21S 6/001; F21Y 2101/02; H01K 7/06; A47G 33/0836
USPC ............................................. 362/393; 40/502
See application file for complete search history.

(56) References Cited

U.S. PATENT DOCUMENTS

| | | | |
|---|---|---|---|
| 4,328,534 A | 5/1982 | Abe | |
| 4,551,794 A | 11/1985 | Sandell | |

(Continued)

FOREIGN PATENT DOCUMENTS

| | | |
|---|---|---|
| DE | 102007014689 A1 | 10/2007 |
| DE | 102007014689 B4 | 8/2011 |

(Continued)

OTHER PUBLICATIONS

Korean Intellectual Property Office, "Notification of Transmittal of the International Search Report and the Written Opinion of the International Searching Authority, or the Declaration", PCT Application No. PCT/US2013/033733, dated Jan. 27, 2014.

*Primary Examiner* — Tracie Y Green
(74) *Attorney, Agent, or Firm* — Fish & Tsang LLP (57) ABSTRACT

Various embodiments of electric lights are described, including those capable of being inserted and powered by a light socket. The electric lights can include a base that can be rotatably coupled to a housing coupled to the base. A flame element can at least partially extend from the housing and be illuminated via a light source that is configured to emit light on to an outer surface of the flame element.

20 Claims, 6 Drawing Sheets

(51) Int. Cl.
  *F21W 121/00* (2006.01)
  *F21Y 101/02* (2006.01)
  *F21Y 113/00* (2016.01)
  *F21K 99/00* (2016.01)
  *A61L 9/03* (2006.01)

(52) U.S. Cl.
  CPC ........ *F21W 2121/00* (2013.01); *F21Y 2101/02* (2013.01); *F21Y 2113/005* (2013.01)

(56) References Cited

U.S. PATENT DOCUMENTS

| | | | |
|---|---|---|---|
| 5,327,332 A | 7/1994 | Hafemeister | |
| 5,664,879 A * | 9/1997 | Lai | 362/392 |
| 6,981,786 B2 | 1/2006 | Yao et al. | |
| 7,159,994 B2 | 1/2007 | Schnuckle et al. | |
| 7,182,489 B2 | 2/2007 | Yao et al. | |
| 7,261,455 B2 | 8/2007 | Schnuckle et al. | |
| 7,837,355 B2 | 11/2010 | Schnuckle | |
| 8,235,558 B1 | 8/2012 | Lauer | |
| 8,777,465 B2 * | 7/2014 | Patton et al. | 362/393 |
| 2006/0028828 A1 | 2/2006 | Phillips | |
| 2006/0034100 A1 | 2/2006 | Schnuckle et al. | |
| 2006/0198164 A1 | 9/2006 | Ronn et al. | |
| 2006/0232958 A1 | 10/2006 | Chang | |
| 2007/0127249 A1 | 6/2007 | Medley et al. | |
| 2007/0223216 A1 | 9/2007 | Jensen et al. | |
| 2008/0198595 A1 * | 8/2008 | Lai | 362/234 |
| 2011/0019422 A1 | 1/2011 | Schnuckle et al. | |
| 2012/0300459 A1 | 11/2012 | Hau et al. | |

FOREIGN PATENT DOCUMENTS

| | | |
|---|---|---|
| DE | 202011109285 U1 | 3/2012 |
| JP | 6-52709 | 2/1994 |
| JP | 2005-78809 | 3/2005 |
| JP | 2005-323866 A | 11/2005 |
| JP | 2012-89462 | 5/2012 |
| WO | 2006/020839 | 2/2006 |
| WO | 2012/162538 | 11/2012 |

\* cited by examiner

ELECTRIC CANDLE HAVING A PLURALITY OF LIGHTS FOR SIMULATION OF A FLICKERING FLAME

This application is a continuation-in-part application of U.S. utility application having Ser. No. 13/850,011 filed on Mar. 25, 2013, which claims the benefit of priority to U.S. provisional application having Ser. No. 61/714,635 filed on Oct. 16, 2012. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is electric lights.

BACKGROUND

The following background discussion includes information that may be useful in understanding the present invention. It is not an admission that any of the information provided herein is prior art or relevant to the presently claimed invention, or that any publication specifically or implicitly referenced is prior art.

Although a variety of electric lights are known in the art, more recently effort has been made to utilize electric lights to simulate a candle, and specifically, a flickering flame effect of a candle whether capable of being inserted into a light socket or stand-alone devices.

Examples of flameless candle devices capable of being powered via a light socket are described in U.S. Pat. No. 4,328,534 to Abe, DE utility model no. 202011109285 to Abel, et al., U.S. Pat. No. 8,235,558 to Lauer, WIPO publ. no. 2012/162538 to WM. B. Coleman Co., Inc., and U.S. pat. publ. no. 2012/0300459 to Hau et al. (publ. November 2012). However, such devices fail to produce a realistic flame effect and suffer from one or more disadvantages including, for example, lacking a realistic flame element and lacking the ability to orient a face of the flame element while the device is inserted into a light socket.

In an attempt to address some of these issues, various manners of generating a realistic flame effect have been explored. See, e.g., U.S. Pat. No. 7,159,994 to Schnuckle, et al., U.S. Pat. No. 7,261,455 to Schnuckle, et al., WIPO publ. no. 2006/020839 to Disney Enterprises, Inc. (publ. February 2006), U.S. Pat. No. 7,837,355 to Schnuckle, U.S. Pat. No. 8,070,319 to Schnuckle et al., U.S. Pat. No. 8,132,936 to Patton et al., and U.S. Pat. No. 8,342,712 to Patton et al. However, among other limitations, such devices also lacking the ability to orient a face of the flame element while the device is inserted into a light socket.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Thus, there is still a need for electric lighting devices that provide for a realistic flame effect that can be oriented to face a user while the devices are inserted into light sockets.

SUMMARY OF THE INVENTION

The inventive subject matter provides apparatus, systems and methods for embodiments of electric lights that simulate a flickering flame effect. Preferred electric lights include a base capable of being electrically coupled to a light socket. It is contemplated that the light socket could be a standard light socket such as an Edison screw socket, or could be other commercially used light sockets including, for example, a bi-pin receiver, a bayonet mount, and a wedge base.

The electric light can further include a housing coupled to the base, and a flame element that at least partially extends from the housing. A light source can be used to emit light on to an outer surface of the flame element. Although the light source is preferably disposed within the housing, it is contemplated that the light source could be disposed at least partially, or entirely, out of the housing.

It is especially preferred that the housing is rotatably coupled to the base such that the housing can rotate with respect to the base, and while the base is coupled to the light socket. In this manner, a face or front surface of the flame element can be oriented while the base is electrically coupled to the light socket (i.e., without requiring rotation of the base), which advantageously allows for a user to position the flame element such that the device's flickering flame effect is viewable from a desired location.

Exemplary electric lights can be formed in four or eight inch versions, although the specific length of the light bulbs can be varied depending on the specific application.

In some contemplated embodiments, the housing can have an electrical connector to a base, which could be configured to plug into base as well as a charging station. It is further contemplated that the housing could include a battery, which allows the electric light to be powered when not connected to a power source. Thus, in this fashion, the electric candle could act as an emergency light source, such that it automatically is illuminated when disconnected from a power source.

In some contemplated embodiments, the light source could predominantly emit first and second wavelengths of light that differ by at least 50 nm. As used herein, the terms "predominant" and predominantly" refer to the peak intensity of a band of wavelengths emitted by a light source. Emitting distinct wavelengths of colors is advantageous as the various colors of light emitted by the lights can collectively and more realistically imitate the true colors of a flame. In addition, the use of different colors of lights could be used to vary a lighting of the flame element, and the light sources could be directed to change randomly, periodically, upon an external signal such as that of a remote computer, or upon the occurrence of one or more triggering events including, for example, detection of users, fluids, music or other sounds, or any combinations thereto.

Various objects, features, aspects and advantages of the inventive subject matter will become more apparent from the following detailed description of preferred embodiments, along with the accompanying drawing figures in which like numerals represent like components.

DETAILED DESCRIPTION

It should be noted that the inventive subject matter may employ various computing devices including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In FIGS. 1A-1D, an embodiment of an electric light 100 is shown having a tall, slender, elongated housing 102 with a base 104 on one end that is configured to be received into, and thereby electrically couple to, a light socket (not shown). Although base 104 is shown having a helical screw 106 on an outer surface of base, such that the base 104 can mate with an Edison screw socket, it is contemplated that the base 104 could be configured to mate with any commercially suitable light socket including, for example, a bi-pin receiver, a bayonet mount, and a wedge base.

Figure 1A:
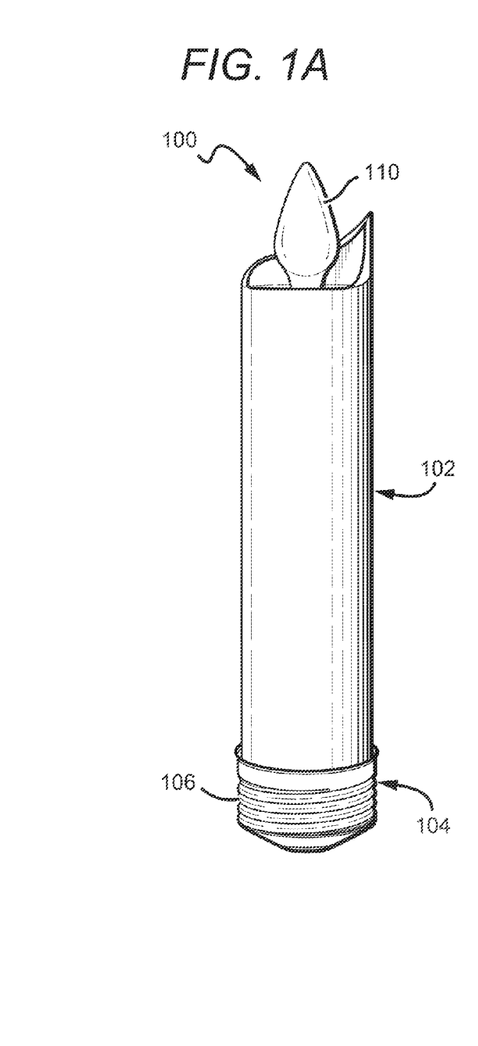
FIGS. 1A-1D are perspective views of one embodiment of an electric light, where a first light source is off in FIG. 1A, a first light source in illuminated in FIG. 1B, and a second light source is illuminated in FIGS. 1C-1D.
Figure 1B:
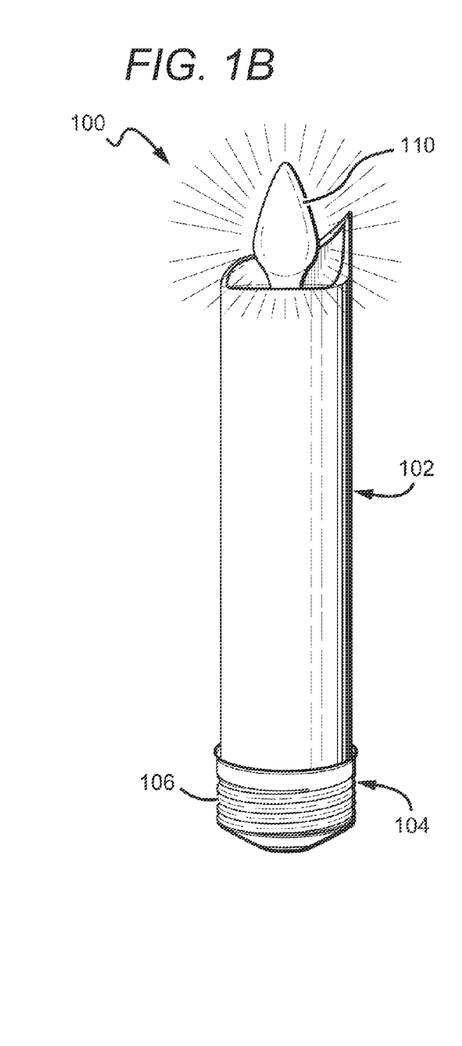

On an opposing end, the electric light 100 can include a flame element 110 onto which light from a light source (not shown) can be projected, thereby illuminating at least a portion of the flame element as shown in FIG. 1B. The flame element 110 may or may not be movable with respect to the housing 102. In embodiments where the flame element 110 is movable, it is contemplated that the flame element 110 could be caused to be moved using one or more drive mechanisms, including, for example, an electromagnetic coil, a fan or other device for moving air or other fluid, and a motor. Different manners for generating flickering flame effects are discussed in U.S. Pat. No. 7,159,994 to Schnuckle, et al., U.S. Pat. No. 7,261,455 to Schnuckle, et al., WIPO publ. no. 2006/020839 to Disney Enterprises, Inc. (publ. February 2006), U.S. Pat. No. 7,837,355 to Schnuckle, U.S. Pat. No. 8,070,319 to Schnuckle et al., U.S. Pat. No. 8,132,936 to Patton et al., and U.S. Pat. No. 8,342,712 to Patton et al.

The light source is preferably disposed to emit light on to at least a portion of the flame element 110. The light source can include one or more, and in some embodiments, two or more lights, each of which independently or simultaneously emit light on to at least a portion of the flame element 110.

Figure 1C:
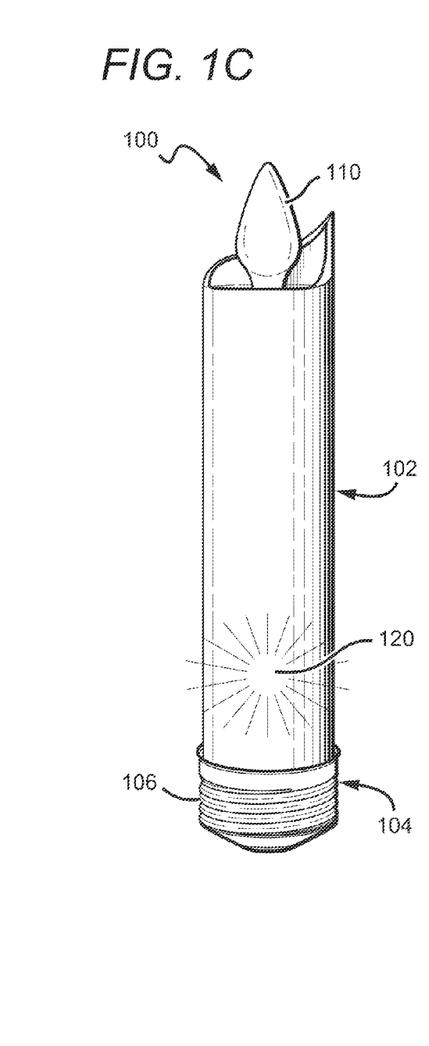
Figure 1D:
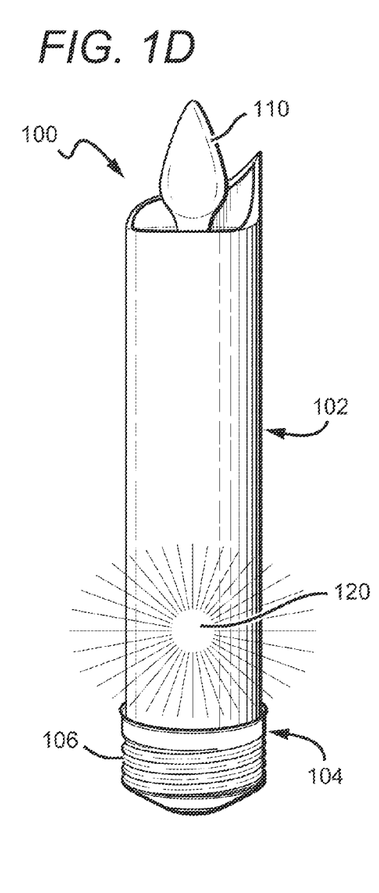

In preferred embodiments, shown in FIGS. 1C-1D, the electric light 100 can also include a second light source 120 distinct and independently operable from the light source, and that is selected to generate additional light from electric light 100. Thus, for example, the light source could be used to generate the flickering flame effect, while the second light source 120 could be used to generate additional light when desired. It is especially preferred that the second light source 120 be dimmable. For example, the second light source 120 could be controlled through a wall rheostat to vary the amount of light emitted from the second light source 120. It is contemplated that the second light source could be configured to slowly fade, such as by sequentially dimming or turning off one or more lights of the second light source 120 individually or in sets to provide for a more natural lighting effect.

It is contemplated that the second light source 120 could comprise a single light or a set of lights. Although shown disposed within housing 102, it is contemplated that the second light source 120 could be disposed outside of housing 102.

The housing 102 preferably comprises frosted glass, although any commercially suitable material could be used including metals or metal composites, plastics and other polycarbonates, wax, and so forth. Where the second light source 120 is disposed within the housing 102, it is preferred that at least a portion of housing 102 is translucent to thereby allow light from the second light source 120 to be emitted from the housing 102.

Figure 2A:
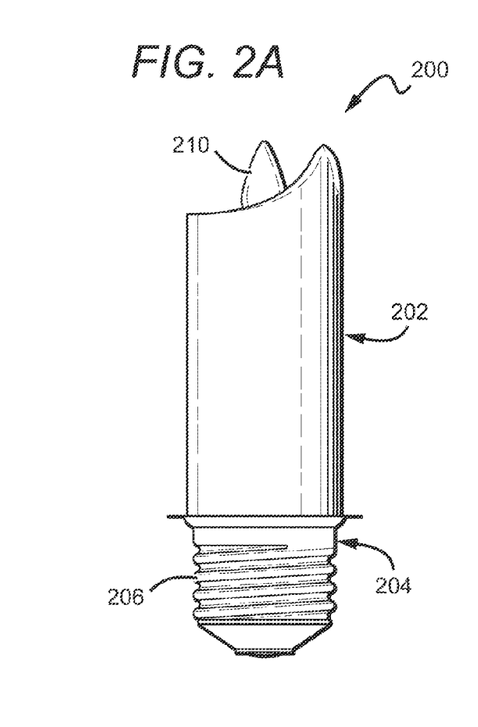
FIGS. 2A-2B are a side view and an exploded view, respectively, of another embodiment of an electric light.
Figure 2B:
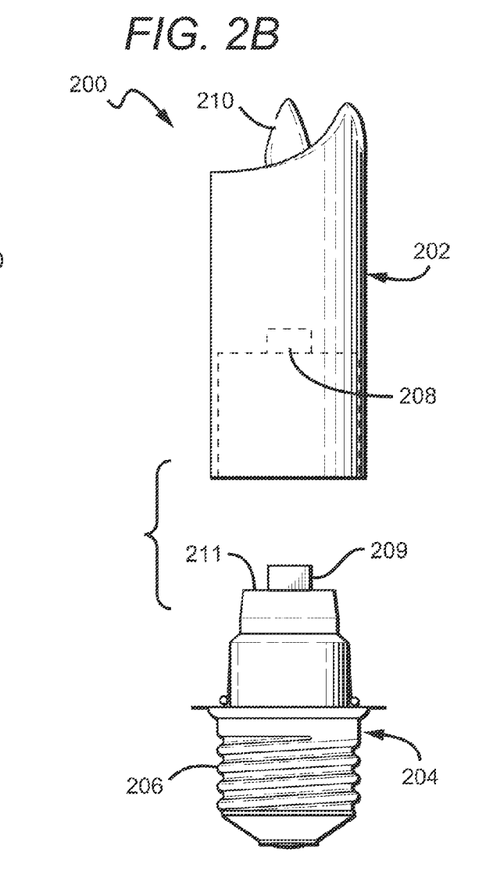

FIGS. 2A-2B illustrate another embodiment of an electric light 200 configured to simulate a flickering flame effect. The electric light 200 can include housing 202 that is coupled to a base 204 having a helical screw 206 on an outer surface of the base 204 to allow the base to be inserted into a standard light socket. Alternatively, the base 204 could be configured to couple with other types of light sockets including, for example, those discussed above.

Electric light 200 preferably includes a flame element 210, which at least partially extends from housing 202. The flame element has a face, which in FIGS. 2A-2B is shown facing to the left. Light from one or more light sources can be emitted on to at least a portion of the flame element 210, and preferably, on to at least a portion of the face of the flame element 210.

It is especially preferred that the housing 202 is rotatably coupled with the base 204, such that the housing can be rotated with respect to base 204, while the base 204 is inserted into (electrically coupled to) a light socket. In this manner, the housing 202 can be rotated without requiring rotation of the base 204, which thereby also reorients a direction of the flame element's face. This is advantageous as it allows the face of the flame element 210 to be properly oriented to provide an optimal flickering flame effect. In the embodiment shown in FIG. 2A, it is desired that the face of the flame element face an observer or a location where observers will most likely view the electric light and its flickering flame effect.

Advantageously, the housing 202 can be rotated approximately 350 degrees and in some embodiments, 360 degrees, with respect to base 204 such that the flame element 210 of the electric light 200 is oriented to a desired direction. The electric light 200 can further include a stop, which can be used to limit rotation of the housing 202 with respect to the base 204, such that upon reaching the stop, the electric light 200 can be inserted or removed from the light socket via rotation of the housing 202. In some contemplated embodiments, the stop can limit the degree of rotation of the housing 202 with respect to the base to approximately 270 degrees.

The housing 202 can include a cavity 208 or other hollow area configured to receive at least a portion 209 of the base 204, as shown in FIG. 2B. Preferably, base 204 includes an electrical connector 211 that electrically couples with a connector disposed within housing 202 to thereby power the electric light 200 via power from the light socket. Alternatively or additionally, a portion of housing 202 could be inserted within base 204 to thereby couple the base 204 to the housing 202. In some embodiments, it is contemplated that the housing 202 can be rotated and/or snapped into the electrical connector 211 to thereby electrically couple the housing 202 with the base 204.

In other contemplated embodiments, the electric light 200 can include an electrical coupling that preferably is at least partially compressible while also electrically conductive. Thus, for example, the bottom portion of base 204 could be composed of an at least partially compressible material, such that the electric light 200 is not required to be fully threaded into a light socket for the electric light 200 to be electrically coupled to the light socket. Rather, as the electric light 200 is rotated within the light socket, the compressible material of the base 204 could be compressed while allowing electricity to be conducted through the base 204 to power the electric light 200. In this manner, the electric light 200 can be rotated as desired, such that the flame element 210 is properly oriented relative to its placement within a room.

It is contemplated that the base 204 and housing 202 could be coupled via a snap-fit, press-fit, screw-in configuration, magnets, or any other commercially suitable fastener(s) or combinations thereof.

Figure 3A:
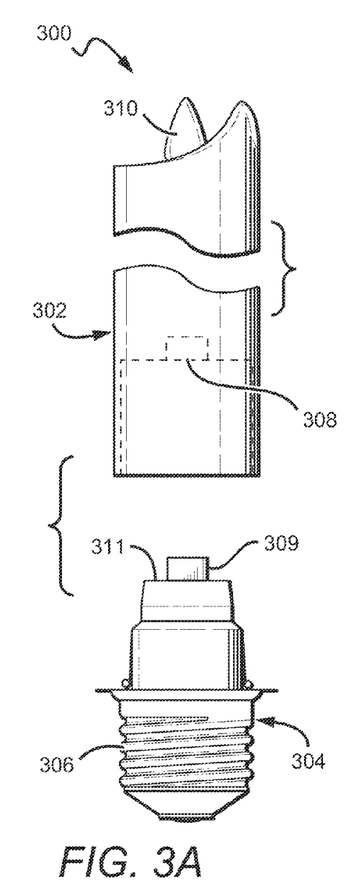
FIGS. 3A-3B are an exploded view and a side view, respectively, of another embodiment of an electric light.
Figure 3B:
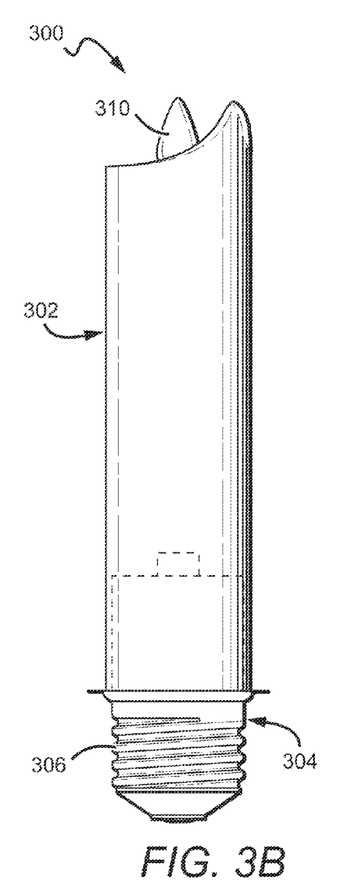

FIGS. 3A-3B illustrate another embodiment of an electric light 300 having a height greater than the height of the electric light shown in FIGS. 2A-2B. With respect to the remaining numerals in each of FIGS. 3A-3B, the same considerations for like components with like numerals of FIG. 2B apply.

Figure 4:
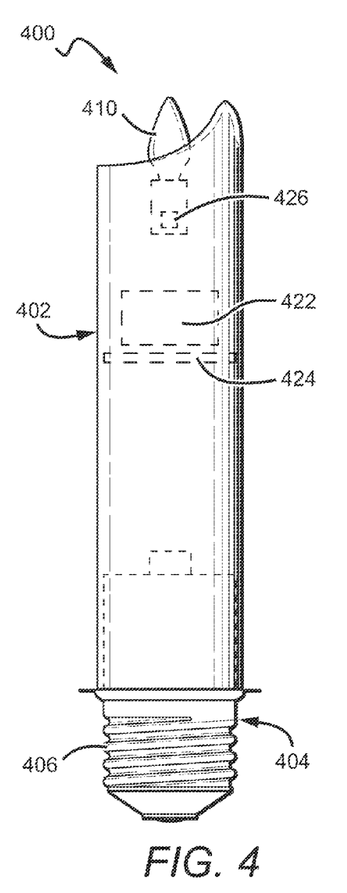
FIGS. 4-5 are side views of additional embodiments of an electric light.

In FIG. 4, another embodiment of an electric light 400 is shown having a flame element 410 that extends from an upper portion of housing 402. Preferably, the flame element 410 is pivotally coupled to the housing 402, which allows the flame element to move with respect to the housing 402. It is contemplated that the flame element 410 can extend through an aperture in an upper portion of the housing 402.

The electric light 400 can include a coil of wire 422 coupled to a signal generator on PCB board 424 to thereby generate an electromagnetic field that can vary over time as electricity passes through the coil. Flame element 410 can include a magnet 426, which interacts with the electromagnetic field thereby causing kinetic motion (movement) of the flame element 410 with respect to housing 402. Alternatively or additionally, flame element 410 could include a ferrous tag or magnetic material capable of interacting with the electromagnetic field.

In other contemplated embodiments, the electric light 400 could include alternative drive mechanisms including, for example, a fan and a motor, sufficient to cause movement of the flame element 410 with respect to housing 402. With respect to the remaining numerals in FIG. 4, the same considerations for like components with like numerals of FIG. 2B apply.

Figure 5:
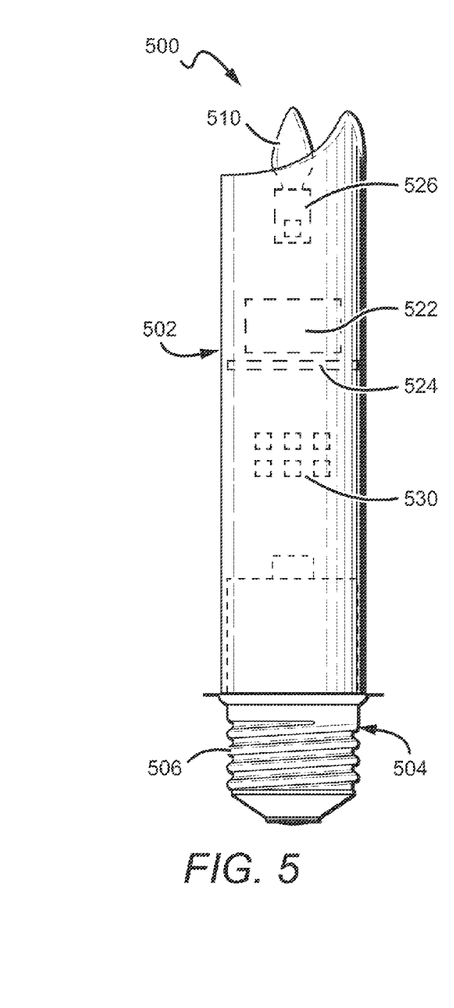

FIG. 5 illustrates another embodiment of an electric light 500, similar to that shown in FIG. 4, except that the electric light 500 includes a second light source 530 disposed within the housing 502 that preferably includes a plurality of LEDs or other lights. In some contemplated embodiments, the second light source 530 can include eight LEDs, although the specific number of LEDs or other light sources can vary depending on the dimensions of the candle, the specific application, the transparency of the candle body, and the amount of light desired. It is especially preferred that the second light source 530 comprises a set of lights that collectively have a brightness that is greater than a brightness of the first light source.

Although the lights are shown grouped together within a portion of the housing 502, it is contemplated that the lights comprising the second light source 530 could be spaced apart and disposed along a length of the housing 502. It is further contemplated that a diffuser or other device that interferes, interrupts, or changes a path of light can be disposed about some or all of the lights of the second light source or disposed within at least a portion of housing 502 to thereby alter the lighting effect produced by the second light source 530.

In other contemplated embodiments, the second light source 530 could be disposed in an upper portion of housing 502, and preferably above the coil of wire 522 or other drive mechanism, such that the second light source 530 can provide additional light from the upper portion of the electric light 500.

The electric light 500 can include a coil of wire 522 coupled to a signal generator on PCB board 524 to thereby generate an electromagnetic field that can vary over time as electricity passes through the coil. Flame element 510 can include a magnet 526 or other magnetic material, which interacts with the electromagnetic field thereby causing kinetic motion (movement) of the flame element 510 with respect to housing 502. With respect to the remaining numerals in FIG. 5, the same considerations for like components with like numerals of FIG. 2B apply.

Figure 6A:
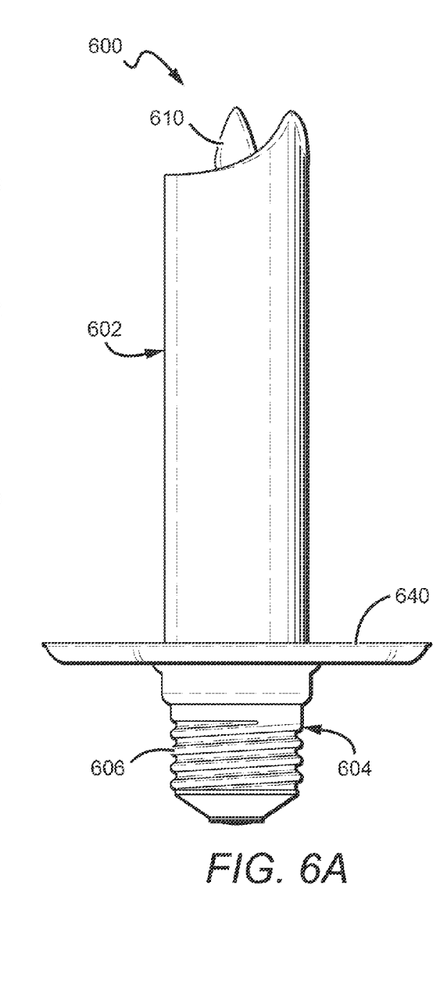
FIGS. 6A-6B are side views of yet another embodiment of an electric light having a second light source disposed on an outer ring.
Figure 6B:
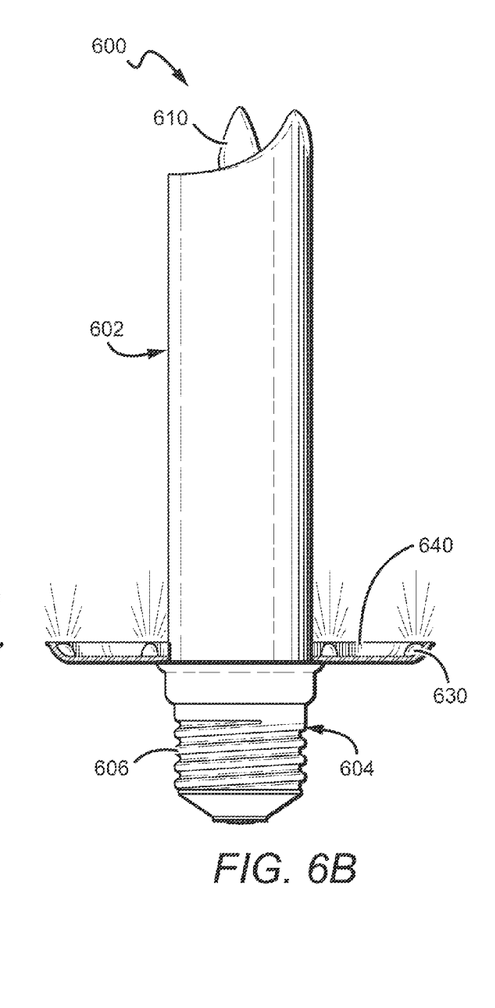

FIGS. 6A-6B illustrates yet another embodiment of an electric light 600 having an outer ring 640 about at least a portion of housing 602 to provide the appearance of a bobeche or drip protector often used with traditional wax candles. In some contemplated embodiments, the outer ring 640 can include a second light source 630 comprising a plurality of LEDs or other lights, as shown in FIG. 6B. It is especially preferred that the second light source 630 is dimmable such that a user can vary the amount of light provided by the second light source 630. With respect to the remaining numerals in each of FIGS. 6A-6B, the same considerations for like components with like numerals of FIG. 2B apply.

Figure 7A:
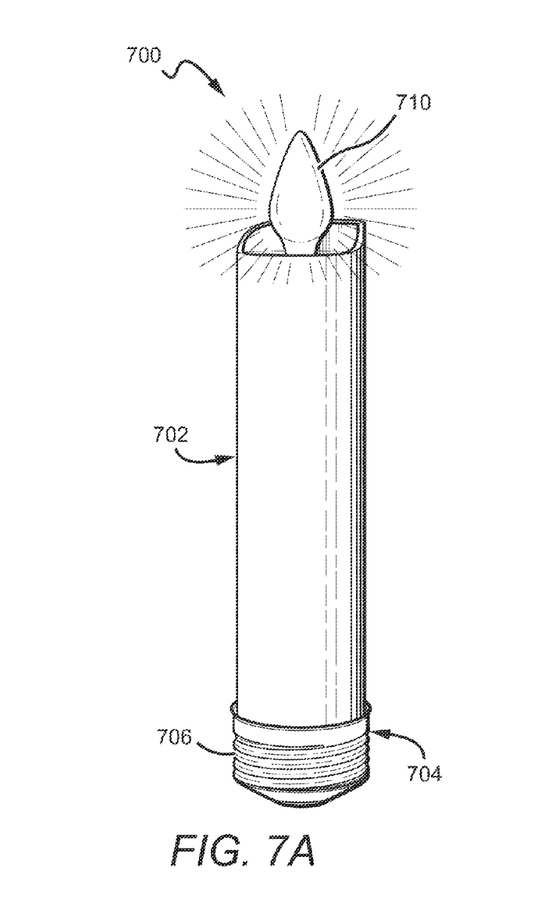
FIGS. 7A-7B are side views of another embodiment of an electric light having a fan and a scent module.
Figure 7B:
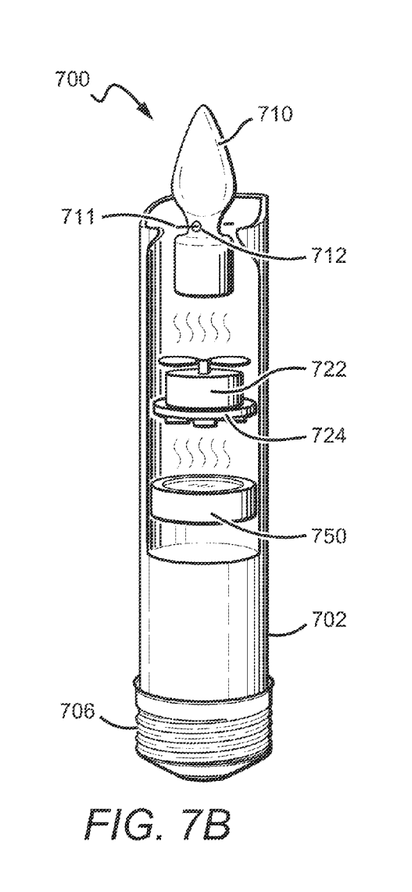

FIGS. 7A-7B illustrates still another embodiment of an electric light 700 having a flame element 710 that extends from an upper portion of housing 702. Preferably, the flame element 710 is pivotally coupled to the housing 702, which allows the flame element 710 to move with respect to the housing 702. In some contemplated embodiments, the flame element 710 can have an aperture 712 through which a support wire 711 may extend. Preferably, a diameter of the aperture 712 is larger than a diameter of the support wire 711 to provide for additional chaotic or random movement of the flame element 710 with respect to housing 702 and the support wire 711. Although shown as a straight wire, support wire could alternatively have a V-shape.

The electric light 700 can further include a fan 722 disposed within the housing 702 and configured such that rotation of the fan 722 causes movement of the flame element 710 disposed above the fan 722 or downstream of air exiting the fan 722. It is further contemplated that the voltage to the fan 722 could be varied over time using circuitry 724 or a controller to thereby cause chaotic movement of the flame element 710, and generate a flickering flame effect using the flame element 710. Such variation may include varying the fan speed over time and/or turning the fan on and off over time.

It is also contemplated that one or more scent modules 750 could be disposed within housing 702, preferably such that airflow caused by fan 722 facilitates release of scent from the scent module. Preferably, the scent modules are user-replaceable, such as by decoupling the housing 702 from the base 704. Where the electric light utilizes an electromagnetic field to generate the flickering flame effect, the scent module could be placed near the coil of wire to thereby heat the scent module and release scent into the atmosphere.

Optionally, the fan 722 can include a weight at the bottom or one of its blades, to vary the effect of the blades' rotation. With respect to the remaining numerals in each of FIGS. 7A-7B, the same considerations for like components with like numerals of FIG. 2B apply.

Figure 8A:
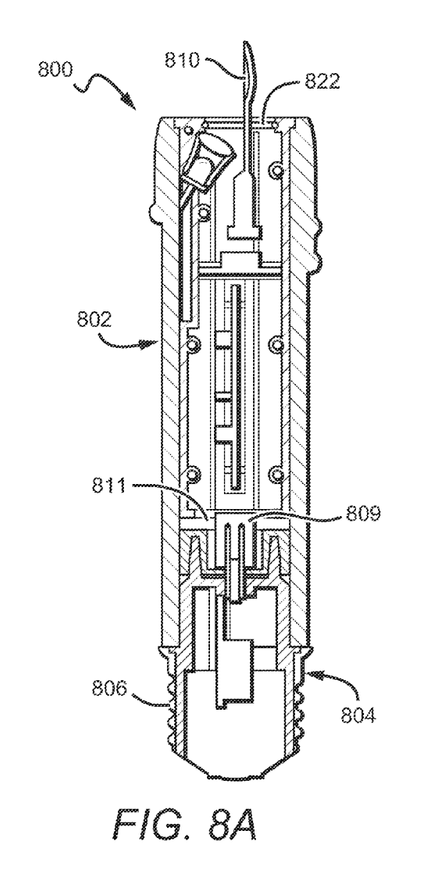
FIGS. 8A-8B are a vertical cross-section view and an exploded view, respectively, of another embodiment of an electric light.
Figure 8B:
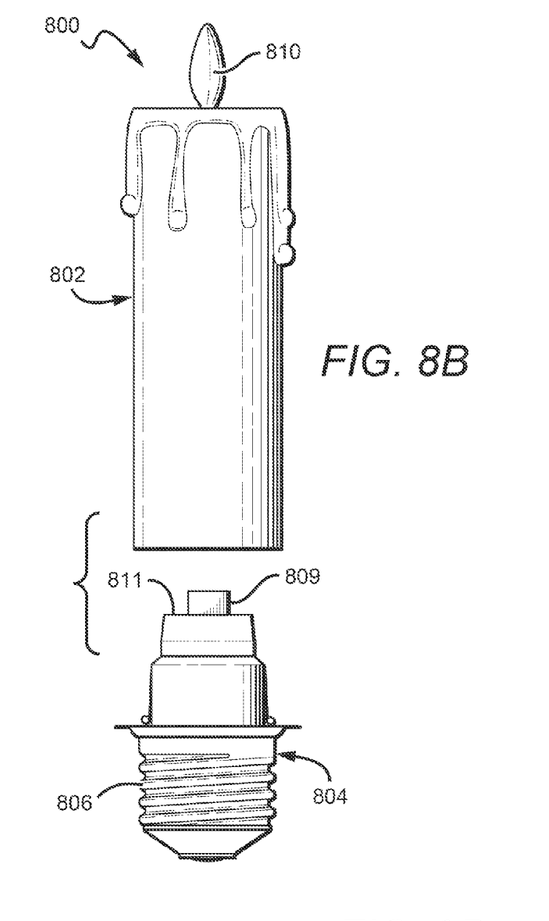

FIGS. 8A-8B illustrate still another embodiment of a electric light 800 having a flame element 810 that extends through an aperture in an upper portion of housing 802. The flame element 810 is preferably mounted on a support wire 811, which extends through an aperture in the flame element 810. A coil of wire 822 can be disposed proximate to an end portion of the flame element 810, which generates an electromagnetic field and causes movement of the flame element 810 via magnet. A light source 803 is disposed to emit light on to the flame element 810.

As shown in FIG. 8B, the flame element 810 preferably has a concavity and therefore is asymmetric. For this reason, the flickering flame effect varies depending on an orientation of a face of the flame element 810 with respect to a viewer. Advantageously, the housing 802 can be rotatably coupled to the base 804, such that the housing can be rotated while the base 804 is coupled to a light socket. In this manner, an orientation of the flame element 810 can be altered after the electric light 800 is properly inserted into a light socket, and thus the flame element can be oriented to maximize the flame effect for a viewer. With respect to the remaining numerals in each of FIGS. 8A-8B, the same considerations for like components with like numerals of FIG. 2B apply.

Figure 9A:
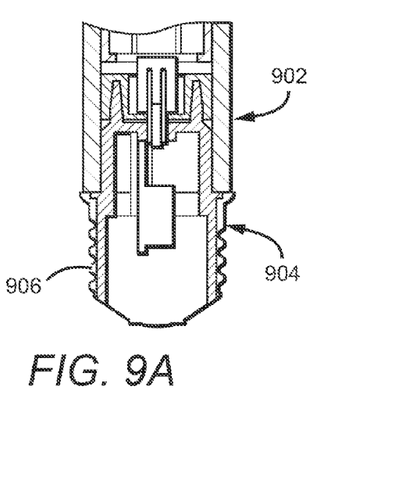
FIGS. 9A-9C are a vertical cross-section view, a close-up view of a portion of FIG. 9A, and an exploded view, respectively, of another embodiment of an electric light.
Figure 9B:
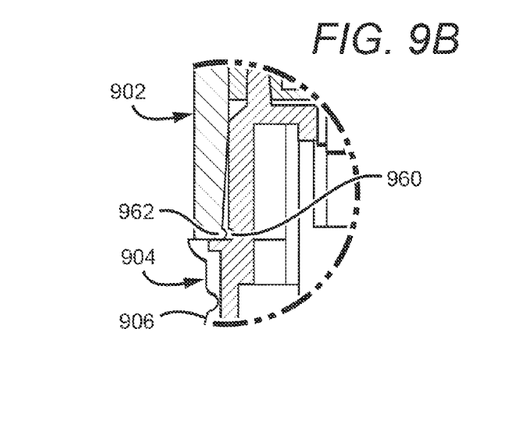
Figure 9C:
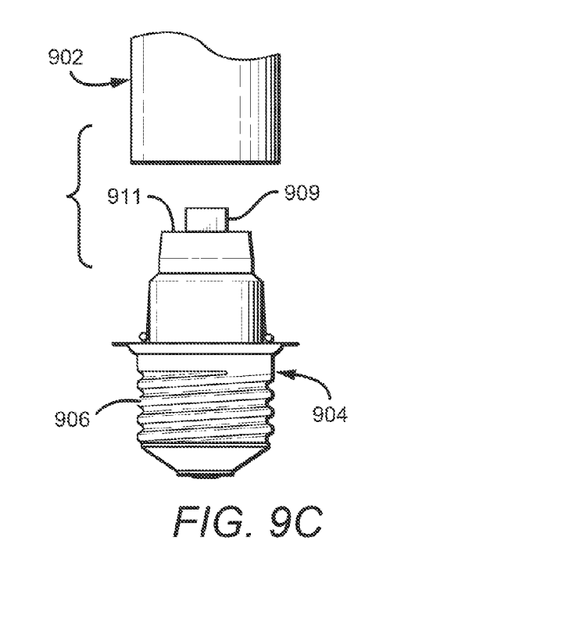

In FIGS. 9A-9C, another embodiment of an electric light 900 is shown in which the housing 902 is coupled to base 904, such that housing 902 can rotate with respect to the base 904. The base 904 can include an indentation 960 into which a projection 962 of housing 902 can be inserted, thereby securing housing 902 to the base 904 while still allowing the housing 902 to be rotated as desired to ensure that a flame element is oriented into a proper position.

Alternatively or additionally, the housing could be rotatably coupled to the base 904, and be secured to the base 904 by rotating the housing in a first direction with respect to the base 904. In such embodiments, base 904 could include one or more stops, such that when a portion of the housing 902 contacts the stop, further rotation of the housing 902 in the first direction allows for the housing and therefore the flame element to be rotated. The stop can also limit full rotation of the housing 902, such as to less than 360 degrees. It is contemplated that the stop could limit rotation to 300 degrees.

In such embodiments, to remove the housing 902 from the base 904, it is contemplated that the housing could be rotated in a second direction opposite of the first direction until a portion of the housing 902 contacts the stop. Upon contacting the stop, it is contemplated that further rotation of the housing 902 with respect to the base 904 would cause the housing to begin separating from the base 904, for example. With respect to the remaining numerals in each of FIGS. 9A-9C, the same considerations for like components with like numerals of FIG. 2B apply.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An electric light, comprising:
  a housing;
  a flame element coupled to the housing, such that at least a portion of the flame element extends from the housing;
  a first light source configured to emit light on to a surface of the flame element; and a second light source disposed with respect to the housing, such that light is emitted on to a side wall of the housing, and wherein the second light source can rotate with respect to the first light source.

2. The electric light of claim 1, wherein the second light source is disposed within the housing such that light is emitted on an inner surface of the housing.

3. The electric light of claim 1, wherein the second light source is disposed outside of the housing.

4. The electric light of claim 3, wherein the second light source is disposed about an outside ring coupled to the housing.

5. The electric light of claim 1, further comprising a set of lights that includes the second light source, wherein the set of lights collectively generate a greater amount of visible light than that of the first light source.

6. The electric light of claim 1, wherein the second light source has a variable brightness.

7. The electric light of claim 6, further comprising a diffuser, and wherein the second light source is disposed within respect to the diffuser such that the diffuser varies the brightness of the second light source.

8. The electric light of claim 1, wherein the housing can rotate with respect to the base, such that a front surface of the flame element is reoriented with respect to the base.

9. The electric light of claim 8, wherein the base is configured to mate with a standard light socket.

10. The electric light of claim 1, further comprising a user-replaceable scent module disposed within the housing.

11. The electric light of claim 1, further comprising a drive mechanism configured to cause movement of the flame element with respect to the housing.

12. The electric light of claim 1, wherein at least a portion of the housing is translucent.

13. The electric light of claim 1, wherein the housing is comprised of glass, metal, wax, or plastic.

14. An electric light, comprising:
a housing;
a flame element coupled to the housing, such that at least a portion of the flame element extends from the housing;
a first set of light sources configured to collectively emit light on to a surface of the flame element; and
a second set of light sources disposed within the housing, such that light is emitted on to an inner surface of the housing, and wherein the second set of light sources can rotate with respect to the housing.

15. The electric light of claim 14, wherein the inner surface of the housing is configured to reflect the light from the second set of light sources onto the flame element.

16. The electric light of claim 14, further comprising a base coupled to the housing, wherein the housing can rotate with respect to the base.

17. An electric light, comprising:
a housing comprising a base;
a flame element coupled to the housing, such that at least a portion of the flame element extends from the housing;
a first light source configured to emit light on to a surface of the flame element; and
wherein the housing can rotate with respect to the base, such that a first surface of the flame element is reoriented while the base is coupled to the housing.

18. The electric light of claim 17, further comprising a drive mechanism configured to cause movement of the flame element with respect to the housing.

19. The electric light of claim 17, further comprising a second light source disposed with respect to the housing, such that light is emitted on to a side wall of the housing.

20. The electric light of claim 19, wherein the second light source is disposed within the housing such that light is emitted on an inner surface of the side wall.

* * * * *